(12) United States Patent
Levovitz et al.

(10) Patent No.: US 11,139,046 B2
(45) Date of Patent: Oct. 5, 2021

(54) DIFFERENTIAL GENE SET ENRICHMENT ANALYSIS IN GENOME-WIDE MUTATIONAL DATA

(71) Applicant: INTERNATIONAL BUSINESS MACHINES CORPORATION, Armonk, NY (US)

(72) Inventors: Chaya Levovitz, Manhattan, NY (US); Laxmi Parida, Mohegan Lake, NY (US); Kahn Rhrissorrakrai, Woodside, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 691 days.

(21) Appl. No.: 15/828,747

(22) Filed: Dec. 1, 2017

(65) Prior Publication Data
US 2019/0171791 A1    Jun. 6, 2019

(51) Int. Cl.
*G16B 5/00* (2019.01)
*G16B 20/00* (2019.01)
(Continued)

(52) U.S. Cl.
CPC .............. *G16B 5/00* (2019.02); *G06F 30/00* (2020.01); *G16B 20/00* (2019.02); *G16B 20/50* (2019.02);
(Continued)

(58) Field of Classification Search
CPC .. A61P 43/00; A61P 35/00; A61P 3/00; A61P 17/00; A61P 37/02; A61P 37/06;
(Continued)

(56) References Cited

U.S. PATENT DOCUMENTS

| 8,577,619 B2 | 11/2013 | Sander et al. | |
|---|---|---|---|
| 2008/0195327 A1* | 8/2008 | Young | C12Q 1/6886 702/20 |

(Continued)

OTHER PUBLICATIONS

Colak (2015) Novel Machine learning models for identification, characterization and prioritization of phenotype-genotype associations. University of Toronto, p. 1-175.*

(Continued)

*Primary Examiner* — Mary K Zeman
(74) *Attorney, Agent, or Firm* — Cantor Colburn LLP; Kristofer Haggerty

(57) ABSTRACT

Embodiments include methods, systems, and computer program products for analyzing genomic data. Aspects include receiving genomic data for an organism, sample phenotypes, and a plurality of gene sets. Aspects include, for each of the gene sets, determining a set of genes G corresponding to genes in the gene set and a set of genes G' corresponding to genes outside the gene set for the phenotypes R and R'. Aspects also include determining a set of mutated genes M and a set of non-mutated genes M' for R and R' and a mutation enrichment score. Aspects also include determining a set of differentiated genes D a set of non-differentiated genes D' for R and R'. Aspects also include identifying an enriched gene set $G_E$ based at least in part upon the mutation enrichment score and the differentiation enrichment score.

14 Claims, 3 Drawing Sheets

(51) Int. Cl.
　　　*G16B 50/00*　　　(2019.01)
　　　*G16B 20/50*　　　(2019.01)
　　　*G06F 30/00*　　　(2020.01)
(52) U.S. Cl.
　　　CPC ....... *G16B 50/00* (2019.02); *C12Q 2537/165* (2013.01)
(58) Field of Classification Search
　　　CPC ............ C12Q 1/6886; C12Q 2600/156; C12Q 2600/106; C12Q 2600/158; C12Q 1/6883; C12Q 1/6827; C12Q 2600/118; C12Q 2600/112; C12Q 2600/172; C12Q 2600/154; C12Q 2600/124; C12Q 1/6809; C12Q 2600/136; C12Q 2537/165; G01N 2800/52; G01N 33/57484; G01N 2800/50; G01N 33/574; G01N 2800/56; G01N 2570/00; G01N 2800/60; G01N 33/5023; G01N 33/6893; G01N 33/5041; G01N 2500/10; G01N 33/5011; G01N 33/5308; G01N 2800/7028; G01N 33/502; G01N 33/6845; G16B 20/00; G16B 20/20; G16B 25/00; G16B 25/10; G16B 30/00; G16B 40/00; G16B 40/10; G16B 40/20; G16B 5/00; G16B 45/00; G16B 35/00; G16B 50/10; G16B 15/30; G16B 30/20; G16B 50/20; G16B 50/30; G16B 20/10; G16B 15/00; Y02A 90/26; G16H 50/20; G16H 50/30; G16H 10/60; G16H 50/70; G16H 20/10; G16H 10/40; G16H 50/50; G16H 70/60; G16H 15/00; G16H 20/30; G16H 40/67; G16H 40/63; G06F 19/325; G06F 17/153; G06F 17/16; G06F 17/18; G06F 16/2465; G06F 16/9024; G06F 2216/03; G06F 3/00; G06Q 40/08; G16C 20/60; Y10S 707/99943; G06K 9/00496; A61K 2300/00; G06N 7/005; G06N 20/00; G06N 20/10; G06N 20/20; G06N 3/0454; G06N 3/084; G06N 5/003; G06N 5/02; G06N 5/04; G06N 7/023; C40B 40/06

See application file for complete search history.

(56) References Cited

U.S. PATENT DOCUMENTS

| | | |
|---|---|---|
| 2010/0210025 A1* | 8/2010 | Wouters ................ G16B 30/00 436/94 |
| 2011/0172929 A1 | 7/2011 | Califano |
| 2013/0060543 A1 | 3/2013 | di Bernardo et al. |
| 2016/0326586 A1* | 11/2016 | Scherer ................. G16B 30/00 |
| 2016/0326593 A1 | 11/2016 | Clement et al. |
| 2017/0076035 A1 | 3/2017 | Califano et al. |

OTHER PUBLICATIONS

Conti, David V., et al. "Using ontologies in hierarchical modeling of genes and exposure in biological pathways." Phenotypes and Endophenotypes: Foundations for Genetic Studies of Nicotine Use and Dependence (2009): 539-584.*

Kowarsch, A. (2010) Correlated mutations: a hallmark of Phenotypic Amino Acid Substitutions. PLOS Computational Biology vol. 6, issue 9, 13 pages.*

Uppu, S. (2016) A Review on methods for detecting SNP interactions in high-dimensional genomic data. IEEE/ACM trans on comp biol and bioinfo, vol. 15 No. 2 p. 599-612.*

Alvarez, M. et al. Functional characterization of somatic mutations in cancer using network based inference of protein activity (2016) Nature Genetics vol. 48 No. 8 p. 838-847; including supplemental information. (Year: 2016).*

Bhat et al. Mesenchymal differentiation mediated by NF-kB promotes radiation resistance in glioblastoma. Cancer Cell (2013) vol. 24: 331-346 and some supplemental information. (Year: 2013).*

Gabriel F. Berriz et al., "Characterizing gene sets with FuncAssociate," Bioinformatics, vol. 19, No. 18, 2003, pp. 2502-2504.

Aravind Subramanian et al., "Gene set enrichment analysis: a knowledge-based approach for interpreting genome-wide expression profiles," Proceedings of the National Academy of Sciences, vol. 102, No. 43, 2005, pp. 15545-15550.

Simina M. Boca et al., "Patient-oriented gene set analysis for cancer mutation data," Genome Biology, vol. 11, No. 11, 2010, R112, 10 pages.

Enrico Glaab et al., "EnrichNet: network-based gene set enrichment analysis," Bioinformatics, vol. 28, No. 18, 2012, pp. i451-i457.

Mariano J.Alvarez et al., "Functional characterization of somatic mutations in cancer using network-based inference of protein activity," Nature Genetics, vol. 48, No. 8, 2016, pp. 838-847.

* cited by examiner

DIFFERENTIAL GENE SET ENRICHMENT ANALYSIS IN GENOME-WIDE MUTATIONAL DATA

BACKGROUND

The present invention relates to genomic data analysis, and more specifically, to differential gene set enrichment analysis in genome-wide mutational data.

Genetic sequencing has become an increasingly available technique for probing the basis for a variety of diseases and disorders. Whole-genome sequencing (WGS) can potentially provide markers or signals indicative of certain phenotypes. For example, some diseases and disorders, such as cystic fibrosis and phenylketonuria, are known to be caused by genomic mutations. Cancer can result from a series of genetic mutations. Both the type and the number of genetic variants and genetic mutations can, in some cases, vary across a population and over time within the population.

SUMMARY

In accordance with embodiments of the invention, a computer-implemented method for analyzing genomic data is provided. A non-limiting example of the method includes receiving, by a processor, genomic data for an organism and sample phenotypes R and R'. The method also includes identifying, by the processor, a collection including a plurality of gene sets, wherein each of the gene sets includes genes associated with an attribute. The method also includes determining, by the processor, for each of the plurality of gene sets, a set of genes G corresponding to genes in the gene set and a set of genes G' corresponding to genes outside the gene set for the phenotypes R and R'. The method also includes determining, by the processor, for each of the plurality of gene sets, a set of mutated genes M and a set of non-mutated genes M' for the phenotypes R and R' and a mutation enrichment score. The method also includes determining, by the processor, for each of the plurality of gene sets, a set of differentiated genes D a set of non-differentiated genes D' for the phenotypes R and R' and a differentiation enrichment score. The method also includes identifying, by the processor, an enriched gene set $G_E$ based at least in part upon the mutation enrichment score and the differentiation enrichment score, wherein the $G_E$ corresponds to the set of genes G that is statistically enriched for D and M in the phenotype R.

In accordance with embodiments of the invention, a computer program product for analyzing genomic data is provided. The computer program product includes a computer readable storage medium readable by a processing circuit and storing program instructions for execution by the processing circuit for performing a method. A non-limiting example of the method includes receiving genomic data for an organism and sample phenotypes R and R'. The method also includes receiving a plurality of gene sets, wherein each of the gene sets includes genes associated with an attribute. The method also includes determining, for each of the plurality of gene sets, a set of genes G corresponding to genes in the gene set and a set of genes G' corresponding to genes outside the gene set for the phenotypes R and R'. The method also includes determining, for each of the plurality of gene sets, a set of mutated genes M and a set of non-mutated genes M' for the phenotypes R and R' and a mutation enrichment score. The method also includes determining, for each of the plurality of gene sets, a set of differentiated genes D a set of non-differentiated genes D' for the phenotypes R and R' and a differentiation enrichment score. The method also includes identifying an enriched gene set $G_E$ based at least in part upon the mutation enrichment score and the differentiation enrichment score, wherein the $G_E$ corresponds to the set of genes G that is statistically enriched for D and M in the phenotype R.

In accordance with embodiments of the invention, a processing system for analyzing genomic data includes a processor in communication with one or more types of memory. The processor is configured to perform a method. A non-limiting example of the method includes receiving genomic data for an organism and sample phenotypes R and R'. The method also includes receiving a plurality of gene sets, wherein each of the gene sets includes genes associated with an attribute. The method also includes determining, for each of the plurality of gene sets, a set of genes G corresponding to genes in the gene set and a set of genes G' corresponding to genes outside the gene set for the phenotypes R and R'. The method also includes determining, for each of the plurality of gene sets, a set of mutated genes M and a set of non-mutated genes M' for the phenotypes R and R' and a mutation enrichment score. The method also includes determining, for each of the plurality of gene sets, a set of differentiated genes D a set of non-differentiated genes D' for the phenotypes R and R' and a differentiation enrichment score. The method also includes identifying an enriched gene set $G_E$ based at least in part upon the mutation enrichment score and the differentiation enrichment score, wherein the $G_E$ corresponds to the set of genes G that is statistically enriched for D and M in the phenotype R.

BRIEF DESCRIPTION OF THE DRAWINGS

The subject matter of the present invention is particularly pointed out and distinctly claimed in the claims at the conclusion of the specification. The foregoing and other features and advantages of the one or more embodiments described herein are apparent from the following detailed description taken in conjunction with the accompanying drawings in which:

DETAILED DESCRIPTION

Figure 1:
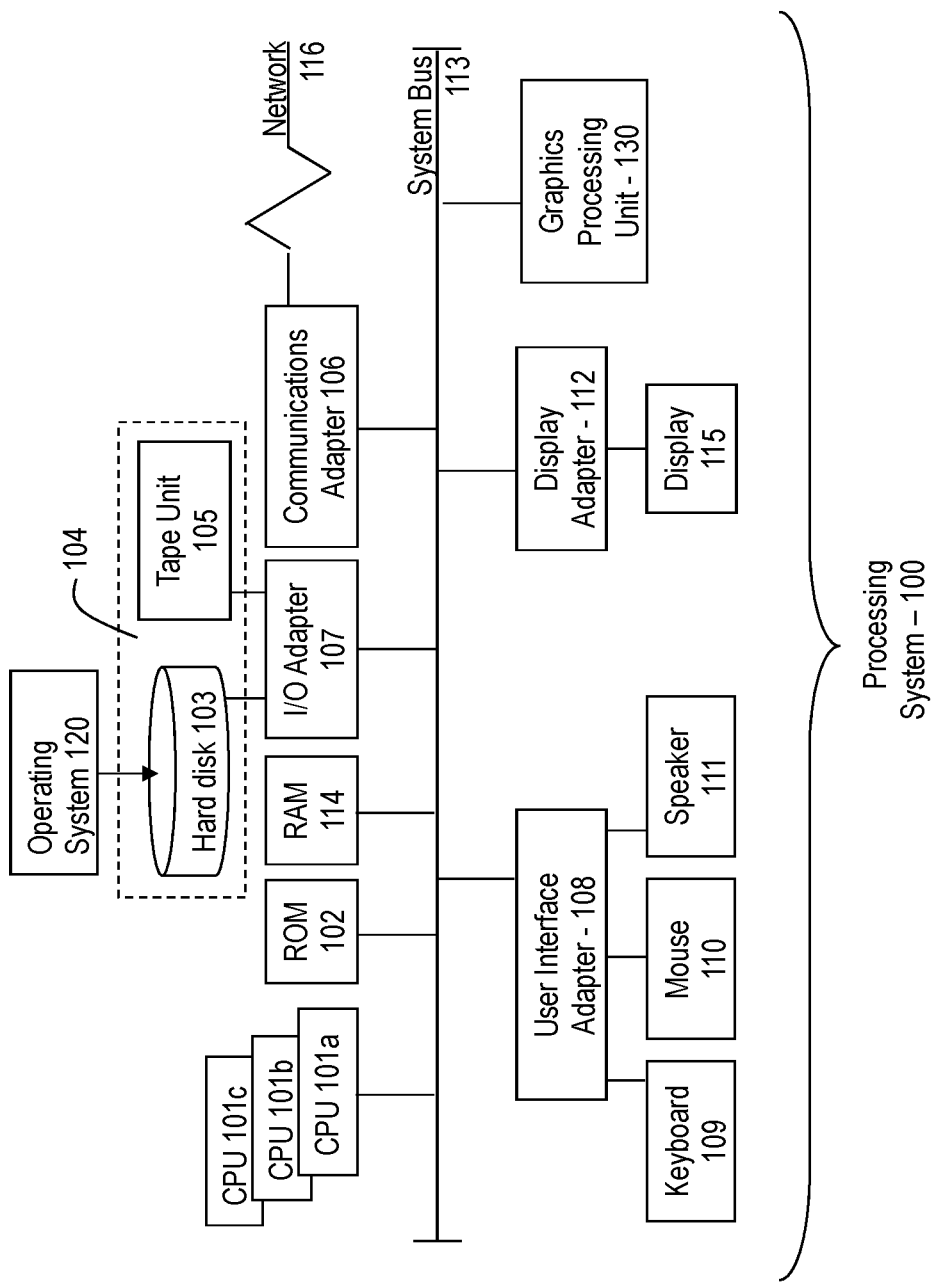
FIG. 1 is block diagram illustrating one example of a processing system for practice of the teachings herein.

Genetic sequences are sought and studied in a variety of contexts and can provide information for the study of phenotype or traits of a population and/or of individuals within a population. Whole genome (WG) datasets include a complete DNA sequence of an organism's genome. Whole exome datasets include the DNA sequences of only the protein coding genes in an organism's genome. SNP datasets are also available, which include datasets directed toward single nucleotide variations that appear at a given genomic site to a certain degree within a population. As used herein, unless otherwise specified, "WG dataset" includes any dataset with mutation information at the gene-level.

Many biological experiments are designed to test differences between two conditions or phenotypes. Such phenotypes can include, for instance, a condition versus the absence of a condition, a trait, or symptom versus the absence or trait of a symptom, or responsiveness or non-responsiveness to a certain treatment, or one trait versus another trait. A comparison of phenotypes that includes a patient's responsiveness or, alternatively non-responsiveness, to a given treatment can potentially provide a rapid and direct improvement on patient outcomes.

A number of phenotypes, including diseases, disorders, and responsiveness to treatment, can be associated with genetic mutations. Such mutations can lead, for example, to pathway regulation or gene expression differences, such as the turning on or off of a gene, expression of mutated proteins, and various other observable or measurable phenotypes. Analysis of genetic mutations themselves can provide valuable information in the study of inherited disorders and certain somatic diseases, such as cancer. Genetic mutation analysis, for instance, has potential to capture information revealed in conventional analyses that focus on observable phenotypes, such as the expression of a mutated protein, but also additional phenotypes that might not be readily observable or apparent.

Yet, reliably uncovering the associations between genetic mutations and related phenotypes is challenging. Cancer, for example, involves abnormal cell growth and is often associated with or caused by genetic mutations. In addition, the genetic material of a tumor or other cancerous tissue frequently acquires more mutations as the tumor grows and can be affected by treatment. Heterogeneity of intra- and inter-tumor samples, as well as patient-to-patient variability, and differing mutation rates between cancer types, differing mutation rates that depend upon treatment, and similar factors complicate analysis of genetic mutations. For example, failure to properly account for inherent imbalances in mutational load between phenotypes of interest can lead to erroneous results. Thus, the identification of consistently altered genes at the genomic level that are statistically significant is challenging.

Turning now to an overview of the aspects of the invention, one or more embodiments of the invention address the above-described shortcomings of the prior art by providing systems and methods that abstract genomic data to the gene set level. By reducing the dimensionality from, for example, 20,000 genes to 500-5000 gene sets, it is possible to identify associated processes for a phenotype of interest. Some embodiments of the invention can evaluate each gene set for an enrichment of mutations within the distribution of mutations within and between phenotypes. Embodiments of the invention can conduct an enrichment analysis based, at least in part, on both phenotype and mutational load differences.

The above-described aspects of embodiments of the invention address shortcomings of the prior art by providing an analysis of differential gene set enrichment in genome-wide mutational data for categorical phenotypes. Some embodiments of the invention can identify statistically significant gene set enrichments for patient cohorts with two phenotypes, such as responsiveness to treatment (R) versus non-responsiveness to treatment (R').

Referring to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 can include a reduced instruction set computer (RISC) microprocessor. Processors 101 are coupled to system memory 114 and various other components via a system bus 113. Read only memory (ROM) 102 is coupled to the system bus 113 and can include a basic input/output system (BIOS), which controls certain basic functions of system 100.

FIG. 1 further depicts an input/output (I/O) adapter 107 and a network adapter 106 coupled to the system bus 113. I/O adapter 107 can be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Software 120 for execution on the processing system 100 can be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which can include a graphics adapter to improve the performance of graphics intensive applications and a video controller. In one embodiment, adapters 107, 106, and 112 can be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which can include, for example, a Super I/O chip integrating multiple device adapters into a single integrated circuit.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 1.

Figure 2:
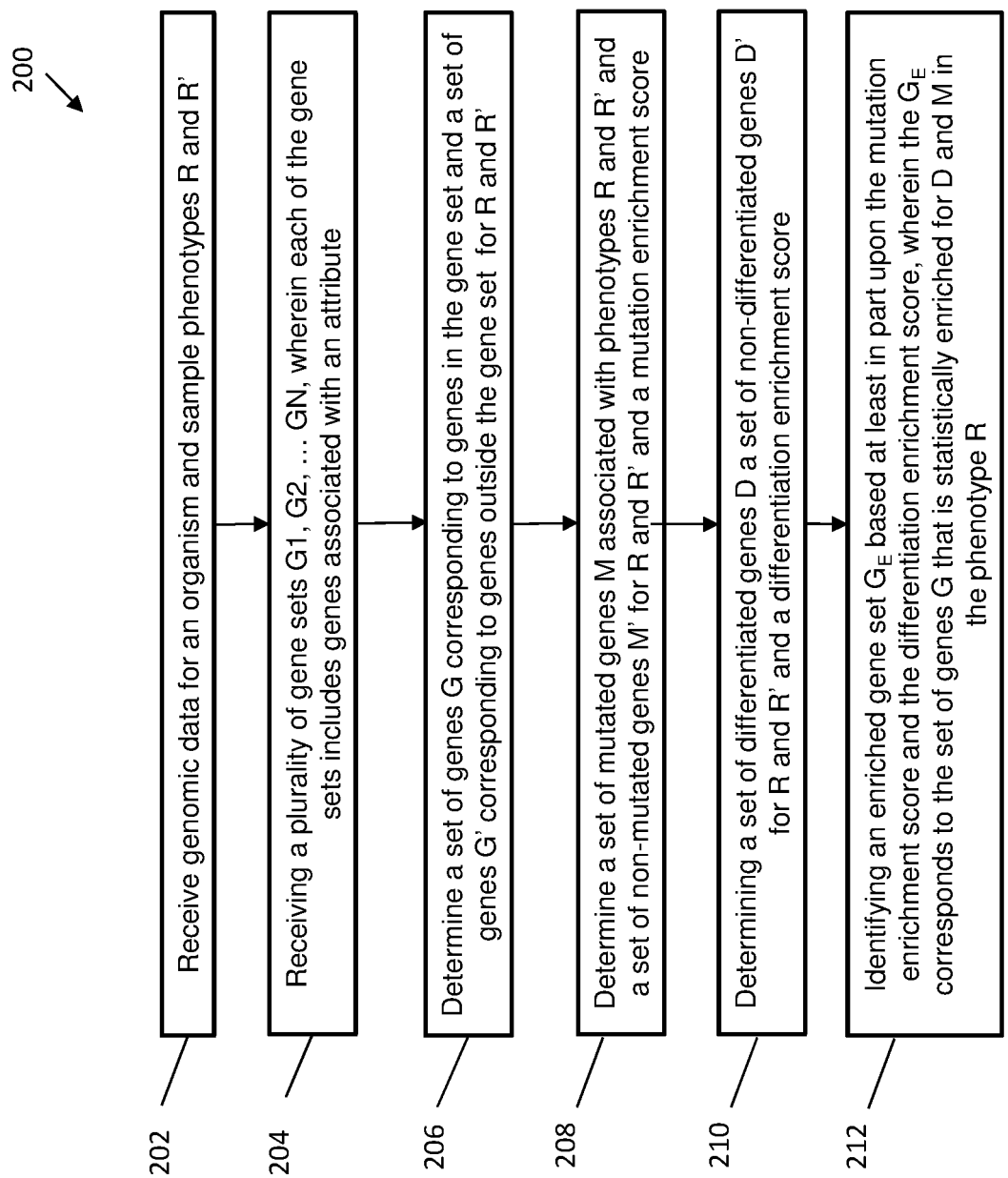
FIG. 2 is a flow diagram illustrating a method for analyzing genomic data according to one or more embodiments of the present invention.

Turning now to a more detailed description of aspects of the present invention, FIG. 2 depicts a flow chart illustrating an exemplary method 200 for genomic analysis. The method 200 includes, as shown at block 202, receiving genomic data for an organism and sample phenotypes R and R'. The method 200 also includes, as shown at block 204, receiving a plurality of gene sets $G_1, G_2, \ldots G_n$, wherein each of the gene sets includes genes associated with an attribute.

Genomic data can include any dataset with mutation information at the gene level. Genomic data can include WGS data, WES data, or NSP data. Methods of acquiring genomic data are known and are not limited by the methods herein. An organism can include, for example, a human, animal, bacteria, fungus, or plant. In some embodiments, the organism is a human. The genomic data can include genomic data for a plurality of organisms, such as a plurality of humans or human patients. In some embodiments, the genomic data is obtained from a known or public collection of data or from combinations of sources. For example data can be obtained from independent patient sets.

Sample phenotypes R and R' can correspond to two phenotypes. R and R' can include any pair of phenotypes of interest. In some embodiments, R corresponds to responsiveness to a treatment and R' corresponds to non-responsiveness to a treatment. R and R' can correspond to any pair of phenotypes. In some embodiments, R and R' are mutually exclusive attributes.

Gene sets can include collections or lists of genes associated with an attribute. For example, a gene set can include known genes associated with a biological pathway, a set of genes associated with similar expression patterns, phenotypes, biological functions, chromosomal locations, or regulation mechanisms. Gene set can be generated or obtained from known sources and by known methods. For example, gene sets can be obtained from MSigDB Geneset Collections, including for instance cytogenetic sets, functional sets, regulatory-motif sets, and/or neighborhood sets.

The method 200 also includes, as shown at block 206, determining a set of genes G corresponding to genes in the gene set and G' corresponding to genes outside the gene set for phenotypes R and R' for each gene set. In some embodiments, determining G and G' includes identifying the set of genes contained in the gene set (G) and all genes outside of the gene set (G') with respect to R and R'.

The method 200 also includes, as shown at block 208, determining a set of mutated genes M associated with phenotype R and R' and a set of non-mutated genes M' for R and R' and a mutation enrichment score.

The method 200 also includes, as shown a block 210, determining a set of differentiated genes D and a set of non-differentiated genes D' for phenotypes R and R' and a differentiation enrichment score. As used herein, "differentiated genes" are understood to mean uniquely mutated genes relative to mutations among the gene set.

In some embodiments, determining an enrichment score includes statistically analyzing mutations M and M', for a mutation enrichment score, and differentiations D and D', for a differentiation enrichment score per each value G and G'. Enrichment scores reflect the statistical significance of an underlying data set.

In some embodiments, methods include determining a mutational load (number of mutations) within a gene L. Mutations M and M' can be represented within L and L'.

In some embodiments of the invention, where $p_i$ is a patient, $g_j$ is a gene, and $k_{ij}$ is a number of mutations in gene $g_j$ of patient $p_i$, $1 \leq i \leq n$ and $1 \leq j \leq m$. A gene $g_j$ can be a loaded gene if $\exists$ some i with $k_{ij} \geq h_j$ for some value $h_j \geq 1$, wherein $h_j$ is a constant for each $g_j$. For example, in some embodiments of the invention, $h_j$ can take the value 3, $\forall j$. In some embodiments of the invention, the value of $h_j$ can differ for different genes based at least in part upon the observed number of mutations of that gene across all patients and/or non-patient data from one or more databases. In some embodiments of the invention $h_j$ is such that when $h_j=1$ gene $g_j$ designates a mutated gene.

In some embodiments of the invention, a gene load $l_j$ for a gene $g_j$ is defined according to one of equations (1), (2) or (3) as follows:

$$l_j = \max\{k_{ij}\}, \quad (1)$$

or $$l_j = \Sigma_i k_{ij} \quad (2)$$

or $$l_j = 1 \quad (3),$$

wherein equations (1) and (2) can associate a data-dependent load to each gene and equation (3) does not attribute load weights to each gene. As can be viewed from above, $h_j$ can determine whether a gene is loaded or unloaded irrespective of $l_j$.

The method 200 also includes, as shown at block 212, identifying an enriched gene set $G_E$ based at least in part upon the mutation enrichment score and the differentiation enrichment score, wherein the $G_E$ corresponds to the set of genes G that is statistically enriched for D and M in the phenotype R.'.

In some embodiments, statistical enrichment scores for gene sets are adjusted for multiple hypothesis testing. A number of methods of adjusting for multiple hypothesis testing are known to persons skilled in the art and include, for instance, the Bonferroni method of adjustment, the Holm adjustment, or the Katz method of calculating bootstrapped estimates of adjusted p-values.

Statistically analyzing mutations M and M' can include constructing contingency tables for each G per R and R' separately as follows:

|    | G | G' |
|----|---|----|
| L  | $\Sigma_{j \in L, G} l_j$ | $\Sigma_{j \in L, G'} l_j$ |
| L' | $\Sigma_{j \in L', G} l_j$ | $\Sigma_{j \in L', G'} l_j$ |

With construction of the contingency table, any two-way statistical analysis can be performed, such as a Fisher's exact test. For example, R and R' can be treated separately and a two-way statistical test can identify which gene sets are significantly enriched within each phenotypic class with respect to that class's mutational background. In some embodiments of the invention, significantly enriched gene sets between R and R' are compared to one other.

Statistically analyzing differentiations D and D' can include identifying $c_j$ such that:

$$c_j = \begin{cases} 11 & \text{if } g_j \text{ mutated in } R \text{ and mutated in } R' \\ 00 & \text{if } g_j \text{ not mutated in } R \text{ and not mutated in } R' \\ 10 & \text{if } g_j \text{ mutated in } R \text{ and not mutated in } R' \\ 01 & \text{if } g_j \text{ not mutated in } R \text{ and mutated in } R' \end{cases}$$

wherein $g_j$ is mutated if loaded according to formula (1) above and differentiated if $c_j=10$ (i.e., it is mutated in R but not in R').

Statistically analyzing differentiations D and D' can include constructing contingency tables for each G per R and R' separately as follows:

|    | G | G' |
|----|---|----|
| D  | D∩G | D∩G' |
| D' | D'∩G | D'∩G'. |

With the above contingency table for D and D' per G and G', any two-way statistical test can be performed, such as a Fisher's exact test. The Fisher's exact test, for example, considers the space of genes uniquely mutated in R and looks for gene sets that are enriched for those uniquely mutated genes.

Figure 3:
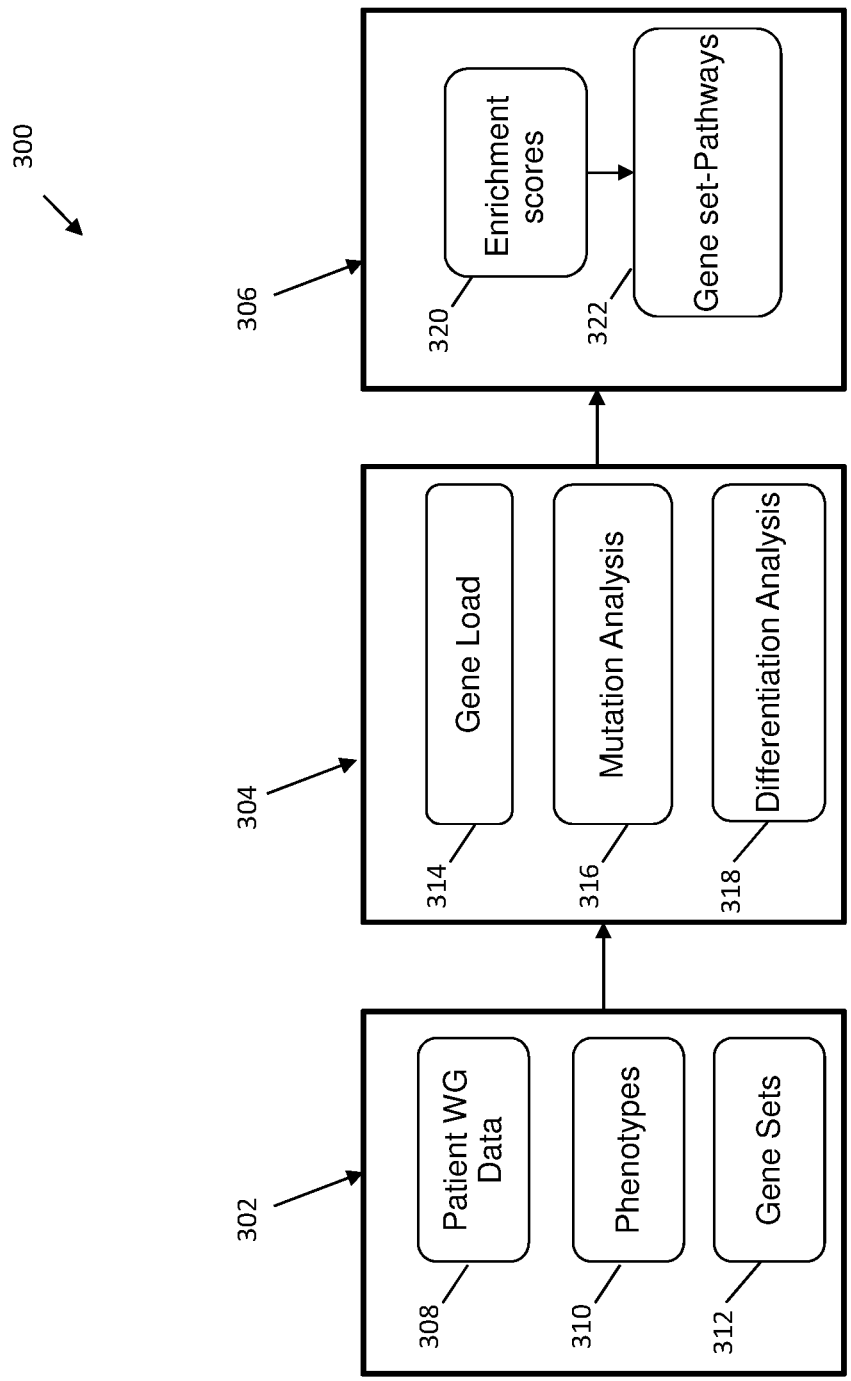
FIG. 3 depicts a diagram illustrating an exemplary system for analyzing genomic data according to one or more embodiments of the present invention.

FIG. 3 illustrates an exemplary system 300 for analyzing genomic data according to one or more embodiments of the present invention. The system 300 includes an input 302, including for instance patient genomic data 308, such as whole genome data, phenotypes 310, and optionally gene sets 312. In some embodiments, a system generates gene sets in a processing system. The system 300 also includes a gene analysis module 304. The gene analysis module 304 can include a gene load determination engine 314 for calculating gene load, a mutation analysis engine 316 for analyzing mutations, and a differentiation analysis engine 318 for analyzing differentiation. The system 300 can include an output 306 including, for example, enrichment scores 320. In some embodiments of the invention, implicated gene-set pathways 322 can be generated and output. For example statistically significant gene sets can be identified based at least in part upon the enrichment scores 320 and can be used to identify one or more implicated gene-set pathways.

Embodiments of the invention can advantageously provide a gene-centric approach to genomic analysis, as opposed to a patient-centric model. Embodiments of the invention can account for high heterogeneity of mutations in patients. For immunotherapy patients, which can have higher levels of genetic mutation, embodiments of the invention can account for the presence of mutational load bias in responders that is documented in the literature. Embodiments of the invention can advantageously reduce false positives through the performance of two-way statistical analyses. Embodiments of the invention test the enrichment of mutations within a gene set with respect to within- and between-phenotype distributions. Moreover, embodiments of the invention can advantageously provide inter-dataset comparison of categorical phenotypes.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments of the invention, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments of the invention, the practical application, the technical improvement over technologies found in the marketplace, or to enable others of ordinary skill in the art to understand the embodiments described herein.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form described. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There can be many variations to this diagram or the steps (or operations) described therein without departing from the spirit of embodiments of the invention. For instance, the steps can be performed in a differing order or steps can be added, deleted or modified. All of these variations are considered a part of the claimed invention.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for analyzing genomic data, the method comprising:
    receiving, by a processor, whole genome data for an organism and sample phenotypes R and R', wherein the phenotype R corresponds to responsiveness to a treatment and the phenotype R' corresponds to non-responsiveness to the treatment;
    identifying, by the processor, a plurality of gene sets that abstract the whole genome data to a gene set level, wherein each of the gene sets includes genes associated with an attribute of a plurality of attributes comprising a same biological pathway, a same expression pattern, a same phenotype, a same biological function, a same chromosomal location, and a same regulation mechanism;
    for each gene set of the plurality of gene sets:
        determining a set of genes G corresponding to genes in the gene set for the phenotype R and a set of genes G' corresponding to genes outside the gene set for the phenotype R;
        determining a set of mutated genes M for the phenotypes R and R' and a set of non-mutated genes M' for the phenotypes R and R', wherein a gene is in M if it is loaded;
        determining a mutation enrichment score that reflects a statistical significance of genes in M and M' by constructing a contingency table for each G per R and R' separately and using a two-way statistical test to identify which gene sets are significantly enriched with respect to a mutational background;
        determining, by the processor, a set of differentiated genes D and a set of non-differentiated genes D' for the phenotypes R and R', wherein a gene is in D if it is mutated in R but not in R';
        determining a differentiation enrichment score that reflects a statistical significance of genes in D and D' by constructing a contingency table for each G per R and R' separately and using a two-way statistical test to identify which gene sets are enriched in a space of genes uniquely mutated in R;
    identifying, by the processor, an enriched gene set $G_E$ comprising the set of genes G that is statistically enriched for D and M in the phenotype R.

2. The computer-implemented method of claim 1, wherein adjusting the identification of $G_E$ comprises the Bonferroni method of adjustment, the Holm method of adjustment, or the Katz method of adjustment.

3. The computer-implemented method of claim 1, wherein the organism comprises a human.

4. The computer-implemented method of claim 1 further comprising determining a mutational load within the M or the M'.

5. The computer-implemented method of claim 1, further comprising identifying a second enriched gene set GE2, wherein the GE2 corresponds to the set of genes G that is statistically enriched for the D and the M in phenotype R'.

6. A computer program product for analyzing genomic data, the computer program product comprising:
   a computer readable storage medium readable by a processing circuit and storing program instructions for execution by the processing circuit for performing a method comprising:
   receiving whole genome data for an organism and sample phenotypes R and R', wherein the phenotype R corresponds to responsiveness to a treatment and the phenotype R' corresponds to non-responsiveness to the treatment;
   receiving a plurality of gene sets that abstract the whole genome data to a gene set level, wherein each of the gene sets includes genes associated with an attribute of a plurality of attributes comprising a same biological pathway, a same expression pattern, a same phenotype, a same biological function, a same chromosomal location, and a same regulation mechanism;
   for each gene set of the plurality of gene sets:
      determining a set of genes G corresponding to genes in the gene set for the phenotype R and a set of genes G' corresponding to genes outside the gene set for the phenotype R;
      determining a set of mutated genes M for the phenotypes R and R' and a set of non-mutated genes M' for the phenotypes R and R', wherein a gene is in M if it is loaded;
      determining a mutation enrichment score that reflects a statistical significance of genes in M and M' by constructing a contingency table for each G per R and R' separately and using a two-way statistical test to identify which gene sets are significantly enriched with respect to a mutational background;
      determining a set of differentiated genes D a set of non-differentiated genes D' for the phenotypes R and R', wherein a gene is in D if it is mutated in R but not in R'; and
      determining a differentiation enrichment score that reflects a statistical significance of genes in D and D' by constructing a contingency table for each G per R and R' separately and using a two-way statistical test to identify which gene sets are enriched in a space of genes uniquely mutated in R; and
   identifying an enriched gene set $G_E$ comprising the set of genes G that is statistically enriched for D and M in the phenotype R.

7. The computer program product of claim 6, wherein adjusting the identification of $G_E$ comprises the Bonferroni method of adjustment, the Holm method of adjustment, or the Katz method of adjustment.

8. The computer program product of claim 6, wherein the organism is a human.

9. The computer program product of claim 6, wherein the method further comprises determining a mutational load within the M or the M'.

10. The computer program product of claim 8, wherein the method further comprises identifying, by the processor, a second enriched G, wherein the second enriched G is the G that is statistically enriched for D and M in phenotype R'.

11. A processing system for analyzing genomic data, comprising:
   a processor in communication with one or more types of memory, the processor configured to perform a method comprising:
   receiving whole genome data for an organism and sample phenotypes R and R', wherein the phenotype R corresponds to responsiveness to a treatment and the phenotype R' corresponds to non-responsiveness to the treatment;
   receiving a plurality of gene sets that abstract the whole genome data to a gene set level, wherein each of the gene sets includes genes associated with an attribute of a plurality of attributes comprising a same biological pathway, a same expression pattern, a same phenotype, a same biological function, a same chromosomal location, and a same regulation mechanism;
   for each gene set of the plurality of gene sets:
      determining a set of genes G corresponding to genes in the gene set for the phenotype R and a set of genes G' corresponding to genes outside the gene set for the phenotype R;
      determining a set of mutated genes M for the phenotypes R and R' and a set of non-mutated genes M' for the phenotypes R and R', wherein a gene is in M if it is loaded;
      determining a mutation enrichment score that reflects a statistical significance of genes in M and M' by constructing a contingency table for each G per R and R' separately and using a two-way statistical test to identify which gene sets are significantly enriched with respect to a mutational background;
      determining a set of differentiated genes D a set of non-differentiated genes D' for the phenotypes R and R', wherein a gene is in D if it is mutated in R but not in R'; and
      determining a differentiation enrichment score that reflects a statistical significance of genes in D and D' by constructing a contingency table for each G per R and R' separately and using a two-way statistical test to identify which gene sets are enriched in a space of genes uniquely mutated in R; and
   identifying an enriched gene set $G_E$ comprising the set of genes G that is statistically enriched for D and M in the phenotype R.

12. The processing system of claim 11, wherein adjusting the identification of $G_E$ comprises the Bonferroni method of adjustment, the Holm method of adjustment, or the Katz method of adjustment.

13. The processing system of claim 11, wherein the method further comprises determining a mutational load within the M or the M'.

14. The processing system of claim 11, wherein the method further comprises identifying a second enriched G, wherein the second enriched G is the G that is statistically enriched for D and M in phenotype R'.

* * * * *